US005586973A

United States Patent [19]
Lemaire et al.

[11] Patent Number: 5,586,973
[45] Date of Patent: Dec. 24, 1996

[54] METHOD AND DEVICE FOR CONTROLLED IRRIGATION AND SUCTIONING OF A LIQUID CLARIFICANT DURING ENDOSCOPIC SURGERY

[75] Inventors: Ivan Lemaire, St Didier au Mont d'Or; Bertrand Gonon, Lyon, both of France

[73] Assignee: C & D Biomedical S.A., Ecully, France

[21] Appl. No.: 353,879

[22] Filed: Dec. 12, 1994

Related U.S. Application Data

[63] Continuation-in-part of Ser. No. 962,210, filed as PCT/FR92/00362, Apr. 22, 1992, abandoned.

[30] Foreign Application Priority Data

Apr. 22, 1991 [FR] France .................................. 91 04969
Apr. 22, 1992 [WO] WIPO .................... PCT/FR92/00362

[51] Int. Cl.⁶ ...................................................... A61M 1/00
[52] U.S. Cl. ................................................ 604/19; 604/31
[58] Field of Search ........................... 604/19, 27–35, 604/65–67, 119; 128/760

[56] References Cited

U.S. PATENT DOCUMENTS

| | | | |
|---|---|---|---|
| 4,184,510 | 1/1980 | Murry et al. | 604/30 |
| 4,261,360 | 4/1981 | Perez | 604/31 |
| 4,795,424 | 1/1989 | Burner | 604/30 |
| 5,141,493 | 8/1992 | Jacobsen et al. | 604/28 |
| 5,178,606 | 1/1993 | Ognier et al. | 604/31 |

Primary Examiner—John D. Yasko
Attorney, Agent, or Firm—Davis, Bujold & Streck, P.A.

[57] ABSTRACT

The irrigation circuit of this apparatus comprises a second pressure sensor CP2 forming a flowmeter with a first CP1, as well as a pressure sensor CPA located downstream.

The apparatus also comprises a processing and control unit UCCG which establishes the calculated value of internal pressure within the cavity PI using the pressure variations furnished by pressure sensors CP1, CP2 during a procedure in relation to the values of the pressure differences during operation outside the cavity, which are stored for each resectoscope RT1... RTi... RTn during an initial calibration phase so that the absorption flow rate can be controlled.

This invention is of interest to manufacturers of surgical instruments.

15 Claims, 8 Drawing Sheets

FIG. 9

WORKING MODES

PRESSURE
CM H$_2$O

IRRIGATION STOPS
POSSIBLE TO EXCEED LIMITS UNDER CONDITIONS OF PHASE 2

UPPER LIMIT = SAFETY PRESSURE
---

AUDIBLE BEEP BS2
TR2
        PHASE 2 = SUCTION INCREASE TO 300 ML/MN
                    IRRIGATION REMAINS LIMITED TO 200 ML/MN
                    PEDAL: IRRIGATION 400 ML/MN
                              SUCTION 500 ML/MN

EXCESS PRESSURE RANGE OR
    CRITICAL WORKING ZONE
---

AUDIBLE BEEP BS1
TR1
        PHASE 1 = IRRIGATION LIMITED TO 200 ML/MN
                    SUCTION LIMITED TO 250 ML/MN
                    PEDAL: IRRIGATION 400 ML/MN
                              SUCTION 500 ML/MN
---

NORMAL WORKING RANGE
AUTOMATIC FLOW SPEED
    REGULATION      VARIABLE SUCTION AND IRRIGATION TO
                                  MAINTAIN PRESSURE WITHIN ZONE OF
                                  TOLERATED PRESSURE
                                  NORMAL FLOW SPEED: 200 ML/MN
                                  PEDAL ACTIVATION AT: 500 ML/MN
---

PRESSURIZATION    IRRIGATION ONLY, SUCTION NIL
                                  PEDAL-ACTIVATED IRRIGATION
---

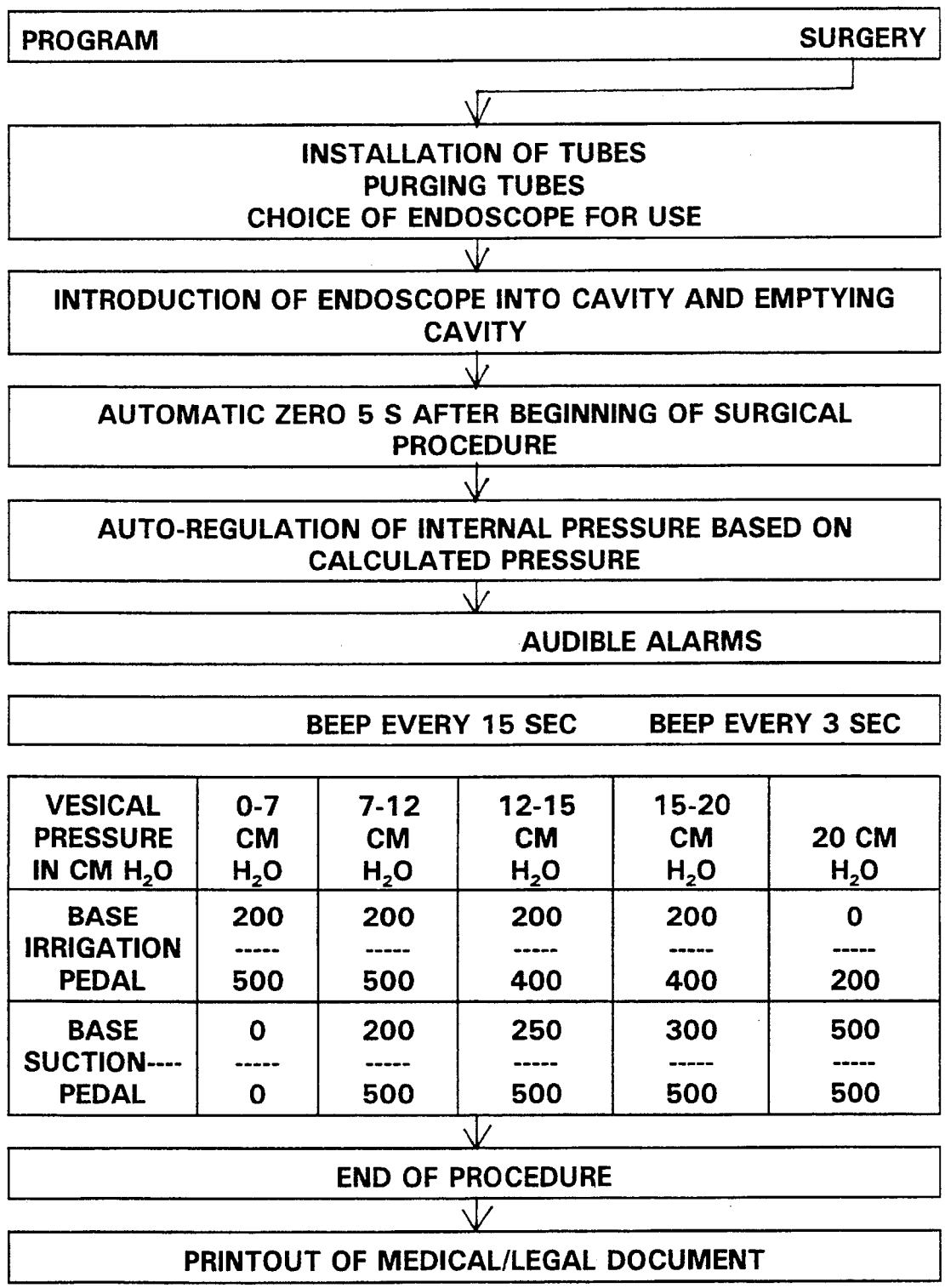

METHOD AND DEVICE FOR CONTROLLED IRRIGATION AND SUCTIONING OF A LIQUID CLARIFICANT DURING ENDOSCOPIC SURGERY

This application is a continuation-in-part of prior patent application Ser. No. 07/962,210, filed as PCT/FR92/00362, Apr. 22, 1992 now abandoned, and fled by the same applicants.

REALM OF THE INVENTION

The invention pertains to endoscopic surgery and more specifically to a device which uses liquid clarificant to irrigate a cavity in a human body and evacuates the clarificant using suction. The cavity either is the actual site or is near the site of surgery being performed with a resectoscope.

A typical application for this device is transurethral prostate resection in which the urinary tract is resected while prostatic tissue is scraped away inside the urethra by means of a blade that moves back and forth on the end of the resectoscope.

TECHNOLOGICAL BACKGROUND OF THE INVENTION

Transurethral prostate resection requires the utmost care to avoid undesirable outcomes, which, in extreme cases, may even include death of the patient.

The main risk is that the circulatory system will absorb the clarificant if internal pressure exceeds a certain limit known as the absorption threshold.

This risk is characterized by acute hemodilution of the surgical patient.

Thus, the surgeon must know the internal bladder pressure and control it constantly in order to modify the flow and suction rate of the irrigation fluid.

Several techniques already exist in the art for controlling distribution and recovery of liquid clarificant evacuated from the cavity of the human body through an endoscope or a resectoscope. Noteworthy among these are U.S. Pat. No. 3,900,022 (WIDRAN) as well as French Patent No. 2.642.297 (SYNERGIE) and European Patent Publication No. 0224487 (BURNER).

The WIDRAN U.S. patent, issued in 1975, relates to the circulation of an isotonic liquid clarificant for a resectoscope throughout the surgical zone. The circuit passing through the resectoscope has an irrigation network consisting of a series beginning with a reservoir and thereafter, a pump, a pressure regulator, a valve, and a pressure indicator and limiter. The suction network comprises the same elements arranged in series, but in the opposite order, leading to a collection device.

Flow is regulated manually through an inlet valve and an outlet valve. The pressure limiter is simply designed to prevent excessive pressure and the pressure regulator is provided to eliminate periodic pressure spurts caused by the peristaltic pump.

This regulator is not assigned to any specific pressure or flow speed in either branch of the circuit. The pressure restriction is merely a safety limit, that is, a cut-off point. The pressure sensor-display is purely visual. It merely displays pressure values during the procedure.

It is apparent that in this invention there is no automatic pressure or flow regulation based upon actual internal pressure within the cavity.

Flow is regulated manually based upon only the pressure displayed, without taking into account the fact that additional blood and urine flow at random during the intervention.

In summary, to be safe, irrigation flow should be controlled only when internal pressure within the cavity is taken into account. Obviously, WIDRAN is unable to either determine or apply this variable governing flow control. WIDRAN's invention takes into account neither the decrease in weight within the circuit and the instrument, nor incoming blood and urine during the procedure, and therefore the displayed pressure fluctuates, varying considerably from the internal pressure.

Regulating flow manually on the basis of the displayed pressure is too inaccurate to be safe for the patient.

Thus, the disadvantages outlined above remain unresolved.

According to the invention described in French Patent No. 2.642.297 filed by the French company SYNERGIE, the resectoscope and therefore the cavity are irrigated with previously heated liquid, the temperature of which is regulated by a thermostatically controlled bath.

This invention is based on the fact that the hemostatic effect desired for coagulation depends upon temperature and that consequently an isotonic liquid which has been heated to a temperature of 42°–45° C. decreases hemorrhaging and thereby the flow rate of the clarificant.

In addition, this invention purports to decrease the risk of absorption of the liquid clarificant by the circulatory system merely by limiting pressure to the maximum regulable value.

Following are some specific characteristics of this invention.

The irrigation network consists of a thermostatically controlled water bath and thereafter, a simple peristaltic pump controlled with a manual keypad. A piezometric cell for measuring excessive pressure is next in the series, followed by a flow regulator and a depression pump. The flow regulator is a throttle-type regulator activated by a pneumatic device which is supplied by the depression pump. The excess pressure control means acts upon the throttle and the peristaltic pump using data from the piezometric cell to control suction and to cut off the irrigation pump if there is excess pressure, i.e., if the pressure exceeds a certain limit.

Two flow sensors, one at the inlet and one at the outlet of the resectoscope, are connected to a processor and a display trait which indicates instantaneous flow rates and differences between them, and also integrates and stores the data to yield a variable for detection of any absorption of the liquid clarificant by the circulatory system. This variable is taken into account in acting upon the pump and the suction flow.

The SYNERGIE invention utilizes the actual pressure value in the suction circuit as an indicator of whether the threshold has been exceeded for stopping the pump. The invention also utilizes the upstream and downstream flow rates in relation to the cavity and the difference between them to determine whether the safety threshold has been attained and to regulate the device.

The above method of regulation and detection by measuring pressure in the suction line and controlling flow fails to ensure perfect vertical pressure control for the following reasons:

there is no way to correct for decreased pressure in the suction line as a function of flow;

it is not possible to measure pressure when the inlet of the resectoscope is blocked by contact with tissue in the urinary tract;

pressure measurement becomes unreliable during frequent gaseous emissions which occur throughout resection when tissues are cut and cauterized. Moreover, because of their design, resectoscopes are often not watertight;

absorption begins once a certain pressure limit is attained—this limit can vary depending upon the flow through the instrument, operating conditions and the patient's morphology; and flow control does not take into account the urine produced by the kidneys during the intervention.

Thus, by failing to correct for pressure loss, a supplementary pressure error is introduced and of the suction inlet is blocked or obstructed as it often is during the surgical procedure, the pressure sensor on the suction circuit is depressed, becoming unreliable or even useless. The system reacts in a disorganized manner to unknown or blocked data and is unable to exert the required control for a certain time period.

Thus the SYNERGIE system cannot continuously monitor the internal, actual pressure within the cavity, which is the only useful basis for regulation, BURNER describes elaborate means for automatically regulating the pumps on the irrigation and suction circuits using pressure within the irrigation and suction circuits and taking into account various pressure corrections such as static pressure and a correction corresponding to pressure loss within the instrument.

Additionally, for safety reasons, when the pressure exceeds a maximum acceptable level controlled by the surgeon, the comparator connected to the control unit stops the irrigation pump and thus the flow of fluid into the instrument or slows the apparatus to minimal functioning level.

The apparatus is completed by a volummetric counter with an audible signal which alerts the surgeon to the flow rate and stops the irrigation fluid when the total predetermined amount required for the process has been used.

The suction branch consists of a circuit similar to the irrigation branch with pressure correction to control the pump on the basis of pressure loss within the instrument, while also taking into account static pressure and providing the same function which limits pressure to the maximum tolerated.

This device provides for pump control based upon a corrected pressure value assumed to be that which prevails inside the cavity, as it relies on the pressure existing at the upstream inlet of the endoscope corrected for pressure loss within the instrument. However, this value is not a reliable or exact indicator of internal pressure due to pulsations and pressure fluctuations coming from the peristaltic pumps required for the apparatus to work with liquids used either to inject the patient internally or for external circulation.

Furthermore, when function is dependent upon such volume values, no allowance is made for body fluids flowing into the cavity, such as blood or mine produced by the kidneys during bladder surgery.

Thus, considerable uncertainty persists and it is possible for absorption into the circulatory system to occur without anyone being aware of it.

BURNER also fails to take into account gaseous emissions which falsify flow rate measurements. The use of an electronic bistoury causes such gaseous emissions dining resection and cauterization.

Finally, BURNER bases his entire theory of real time regulation on an irrigation pump delivering a continuous flow. In his method correction is based upon only one variable signal, which is assumed to be non-undulating. However, to prevent infection and for other reasons of hygiene and prophylaxis, the use of peristaltic pumps is obligatory in the medical field.

Under such conditions, the apparatus of the BURNER patent is not sufficient to provide the permanent, specific information regarding actual interior cavity pressure which is necessary for precise, reliable flow regulation and to ensure the patient's safety.

OBJECT OF THE INVENTION

The object of the present invention is to overcome the disadvantages of the prior art techniques and to provide a complete, reliable solution to the problem of permanently determining and continuously controlling actual, specific pressure within the cavity, for example, vesical pressure, throughout the intervention.

To ensure that the surgeon is relatively at ease while performing the resection and free of the constant concern with maintaining bladder pressure at the ideal level, while at the same time preventing fluid absorption, it is necessary not only to determine the irrigation and suction flow rates outside the bladder and correct for pressure loss, but also to be constantly aware of the actual specific internal bladder pressure, as it is not possible to introduce a pressure sensor into the bladder.

Furthermore, in order to prevent abnormal functioning and avoid having to block the pumps when the suction circuit is partially or totally blocked by tissue removed during the resection, the surgeon must place the extremity of the instrument in the cavity.

In addition, the surgeon must be able to withdraw from the intervention zone to prevent lesions on the striated sphincter and to proceed with his or her work. In retracted position the endoscope can no longer provide suction, as its suction orifice is in contact with the wall of the urinary tract, thereby causing an increase in interior pressure.

These three requirements, which are either not met or only partially met by prior art devices, are fulfilled by the device of the invention in the following manner:

the exact interior bladder pressure is known at all times, having been calculated from the data regarding pressure loss within the irrigation and suction networks, and because various properties of the instrument have been stored in memory before the outset of surgery. The calculation device continuously furnishes exact internal pressure values on the basis of the stored data;

the flow of irrigation fluid can be constantly regulated because the interior cavity pressure is known and the pressure can be brought to an optimal value using the appropriate automatic command on the irrigation and suction pumps. The work zone corresponds to the self-regulating pressure system in which the pressure is regulated by acting upon the suction pump;

pressure spurts caused by withdrawing the endoscope from the operating zone and obstruction of the suction orifice during contact with the adjacent wall or, more rarely, because tissue fragments are introduced, automatically cause higher pressure, whereby the suction rate increases during a first phase and then increases again during a second phase, until a maximum suction flow rate and a pressure limit called the safety limit are attained.

This routine is characterized by a slow, repetitive audible signal in the first phase and a rapid one in the second phase From this point on the surgeon need no longer be concerned with maintaining pressure at a certain value, but may devote himself or herself entirely to performing surgery. The surgeon's mind is now free to concentrate upon such purely medical and surgical parameters as observing patient reactions, working neatly, cauterizing arterioles, and resectoscope performance.

SUMMARY OF THE INVENTION

To accomplish its objectives, the device according to the invention comprises an irrigation network and a suction network, each containing the various active and passive devices and components, a central processor and control unit, computer peripherals such as a screen, a keyboard and a printer, as well as a measurement means which supplies continuous information regarding the weight difference between the fluid delivered by the apparatus for injection into the bladder and the fluid which has been collected.

More specifically, the apparatus encompasses the following functions, elements and devices.

The irrigation and suction networks each consist of a pump, one or more pressure sensors and means for comparing the measured pressures. The irrigation network comprises a second pressure sensor that is connected to the first by a calibrated conduit, thereby forming a flowmeter with the first. The suction network further comprises a conductimetric sensor which monitors bleeding. Two weight differential measurement devices keep track of the amount of fluid flowing into the cavity from within the body.

The device further consists of a processing and control unit which establishes on a permanent basis the calculated pressure value within the cavity on the basis of the difference in pressure furnished by the pressure sensors in the irrigation network and stored in memory during the initial calibration phase in order to control irrigation flow rate and absorption and to maintain internal cavity pressure at an acceptable value, below the absorption threshold.

A pedal is provided for temporarily increasing flow when blood obstructs the field of vision.

In addition, a printer delivers a written report outlining the details of the surgical procedure, specifically pressure values and flow rates.

The object of the instant invention is to provide a totally reliable solution to the problem of continuous awareness and control of the actual, specific cavity pressure, for example, within the bladder.

By automatically regulating flow on the basis of the calculated internal pressure, the device of the invention frees the surgeon from preoccupation with such details and allows him or her to concentrate only on the active surgical process.

The invention consists of gauging the irrigation and suction networks to conform to instruments already existing in the surgical profession (or more generally, in a hospital) so they continuously and in real time furnish information about pressure loss in each branch and can therefore correct for pressure measurements while taking into account the calculated internal pressure, which corresponds precisely to the pressure prevailing within the cavity.

BRIEF DESCRIPTION OF THE DRAWINGS

Technical characteristics and other advantages of the invention will be apparent from the following description, which is presented as a non-limiting example of one embodiment of the invention, with reference to the accompanying drawings, wherein:

FIG. 9 is a table schematically showing the working modes, one of which is the autopressure regulation mode after internal pressure is calculated;

FIG. 12 is a general organizational diagram showing how the apparatus according to the invention functions during a surgical resection.

DETAILED DESCRIPTION OF A PREFERRED EMBODIMENT

Figure 1:
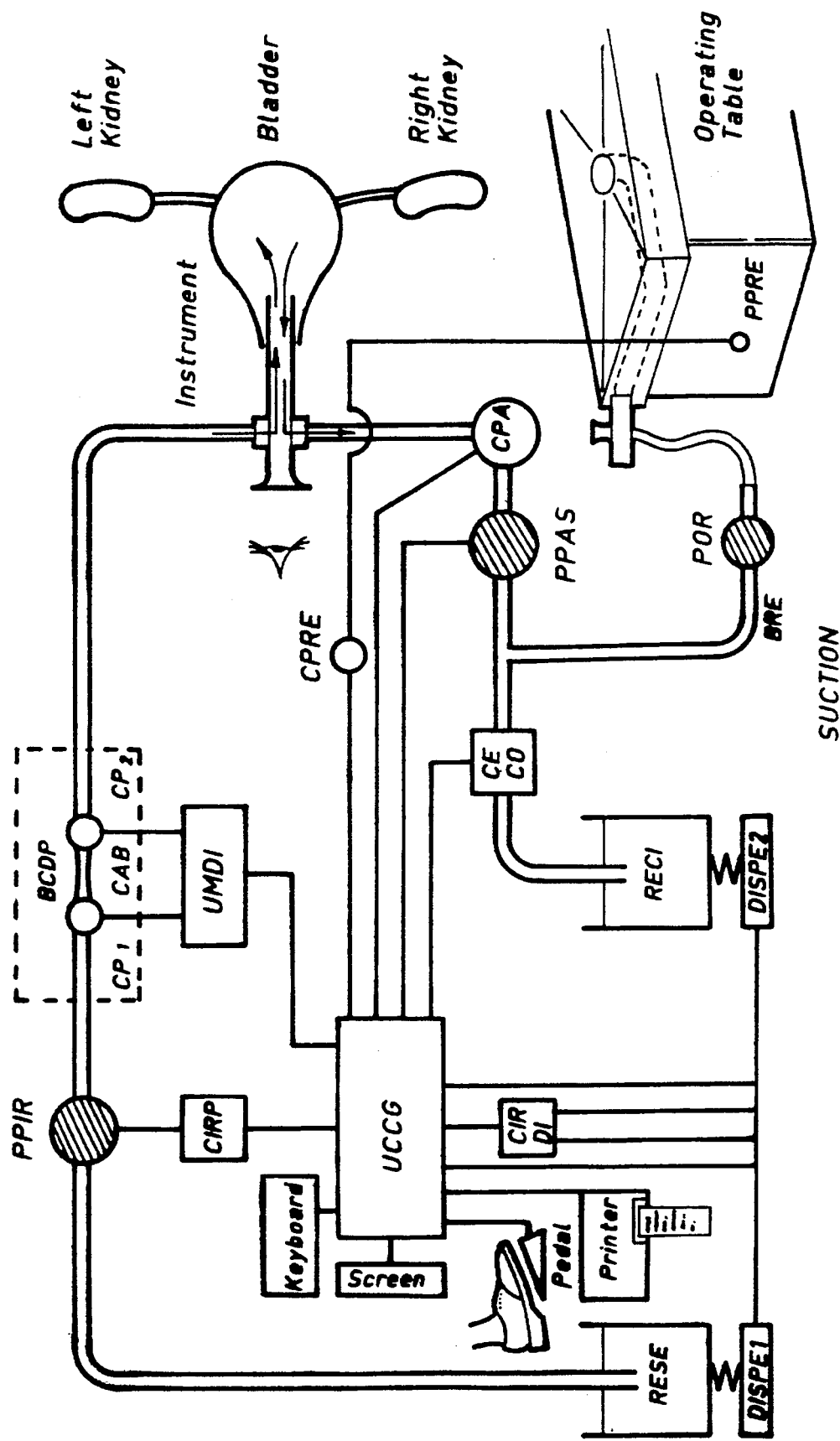
FIG. 1 is a functional schematic drawing of the invention showing the physical arrangement of its components.
Figure 2:
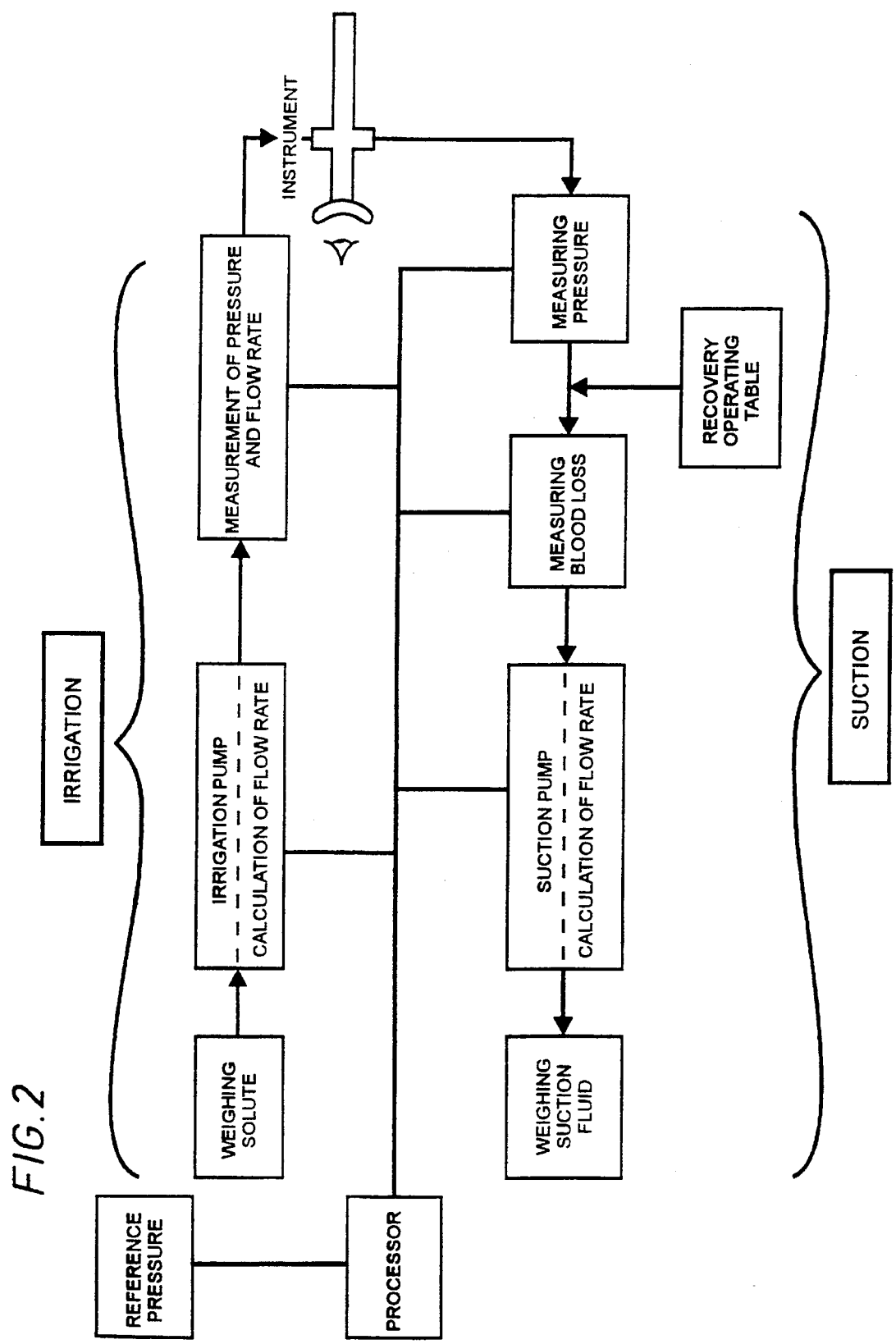
FIG. 2 is a synoptic table showing the general arrangement of the apparatus.

The general purpose of the apparatus shown in FIGS. 1 and 2 is first, irrigation and suctioning through a portion of a dual channel surgical endoscope and second, through a cavity in the human body which comprises the site of surgical intervention or is near that site.

The surgical endoscope will hereafter be referred to by its specific generic name, resectoscope, or by the more general term instrument.

The branch marked IRRIGATION comprises the following functional blocks: a weighing mean for the irrigation solution, a peristaltic irrigation pump with a flow monitor, and a means for measuring the pressure difference between two distant points separated by a calibrated conduit.

The branch marked SUCTION comprises the following functional blocks: a means for measuring suction pressure at the outlet of the instrument, a peristaltic pump with a flow monitor, a means for recovering fluid from the operating table, a means for measuring blood loss, and a means for weighing the suction fluid evacuated.

The system functions according to the original principle of regulating suction flow on the basis of the pressure PI prevailing in the cavity said pressure being calculated by a central processor and control unit UCCG using the CALIBRATION data.

The processor UCCC includes such conventional peripherals as a keyboard, a screen and a printer, as well as a PEDAL which the surgeon can use to instantly elevate the level of irrigation-suction if the surgery requires additional clarificant.

With reference to FIG. 1, which is a schematic representation of the controlled irrigation apparatus according to the invention, note the branch labeled IRRIGATION connected to one of the passages within the instrument and the branch labelled SUCTION connected to the other passage.

Several models of surgical endoscopic instruments that are adaptable for use with the device according to the invention exist in the art. These instruments RT1 . . . RTi . . . RTn have internal conduits of varying diameters and each reacts differently to global pressure loss within the circuit of the device, which is the basis for calculating the actual value of pressure PI within the cavity.

More specifically, the IRRIGATION circuit essentially consists of a peristaltic irrigation pump PPIR and two coupled pressure sensors CP1 and CP2 yielding pressure values P1 and P2. The sensors are connected by a calibrated Venturi conduit CAB. These elements constitute the block for measuring pressure difference, BCDP. The SUCTION circuit essentially consists of a peristaltic suction pump with a flow monitor PPAS and a suction pressure sensor CPA following the suction pump near the outlet of the suction passageway in the instrument.

An associated branch called recovery circuit BRE originates at the collection means on the operating table. This branch contains a recovery pump POR and is connected to the SUCTION circuit below the suction pump PPAS and above the conductimetric cell CECO.

These pumps and pressure sensors are connected to the central processor and control unit UCCG, the main function of which is controlling such parameters as volume and flow rate of both the liquid clarificant to be injected into the cavity or into the surgical zone, and also the volume of fluid suctioned from the cavity, taking into account the actual pressure value PI within the cavity calculated on the basis of pressure variations $\Delta P = P1-P2$ as it functions within and without the cavity, measured by block BCDP surrounding CP1, CAB and CP2, while at the same time controlling and directing the suction rate.

The circuits labelled IRRIGATION and SUCTION further comprise, respectively, a first weighing means DISPE1 and a second weighing means DISPE2 which are used for the contents of reservoir RESE and receptacle RESI, respectively, and the resulting measurements, after differential measurement through a differential circuit CIRDI of conventional design, are used when calculating the volume of incoming fluid.

Finally, the SUCTION circuit has a conductimetric measurement cell CECO for measuring blood flow and calculating blood loss, that is, the amount of incoming blood.

A supplementary pressure sensor, called the reference sensor CPRE, is connected to a pressure point PPRE on the operating table and is also connected to the central processor and control unit. Its purpose is to relate the measurements to a base value. Thus the measurements are all relative to this base value.

Using the data transmitted by the weighing device DISPE1 and the pressure differential value $\Delta P = P1-P2$ between sensors CP1 and CP2, the central processor and control unit UCCG, which has an internal clock, calculates in real time the weight, the volume and the pressure of the irrigation fluid, as well as the flow rate of the irrigation pump. In addition, this unit stores the reference pressure furnished by reference sensor CPRE and the length of time for which the apparatus functions.

As for the suction circuit, the same weight measurements are taken by the individual weighing device DISPE2, and the pressure by means of pressure sensor CPA located below it, and the corresponding results are transmitted to the central processor and control unit UCCG.

A supplemental conductimetric measurement from a cell CECO supplies data on blood loss, that is, bleeding from the quantity of blood in the fluid suctioned from the surgical cavity. Since the weight of the liquid clarificant injected and of the recovered suctioned fluid are known, and also the conductimetric data regarding the recovered suctioned fluid containing blood, the degree of hemodilution can be calculated, that is, the volume of liquid clarificant which has entered the bloodstream.

The central processor/control unit UCCG runs software which provides automatic, global control over the apparatus and regulates it on the basis of the pressure signals from sensors CP1 and CP2, processed as algorithms.

The principles according to which the device functions are as follows.

All other factors being equal, that is, the type of instrument, the difference between the two different modes of use, i.e., using the instrument outside the cavity or using it inside the cavity, has a beating only on the value of internal cavity pressure PI. Therefore, the apparatus is used outside the cavity or with the circuit on the instrument closed to determine the various possible flow rates for an application. The values of pressure loss relative to each flow rate within each branch are stored for each such rate so that when the instrument is used inside the cavity, value PI and its variations can be isolated and regulated by taking the appropriate action on the suction flow rate.

Figure 5:
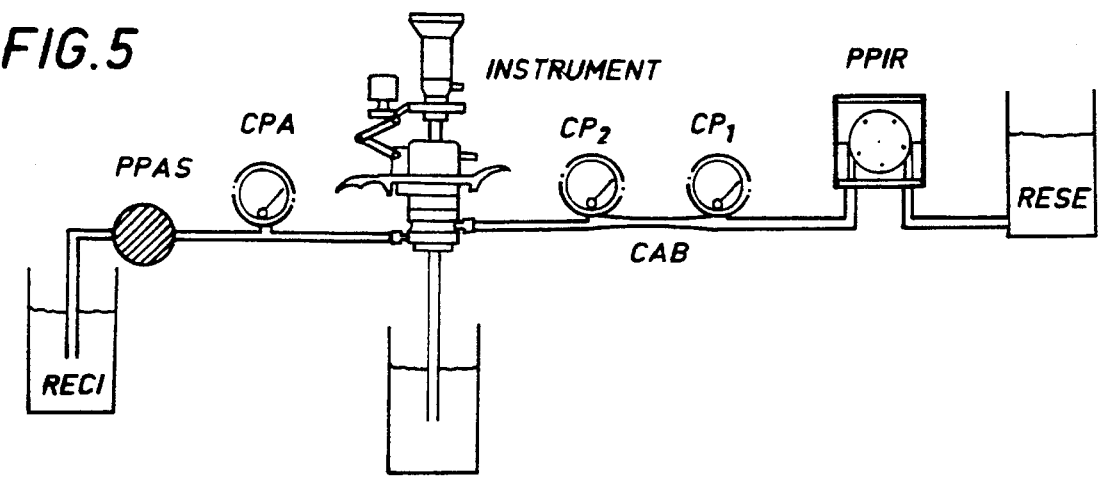
FIG. 5 shows how the apparatus is calibrated for connection to any type of resectoscope.
Figure 6:
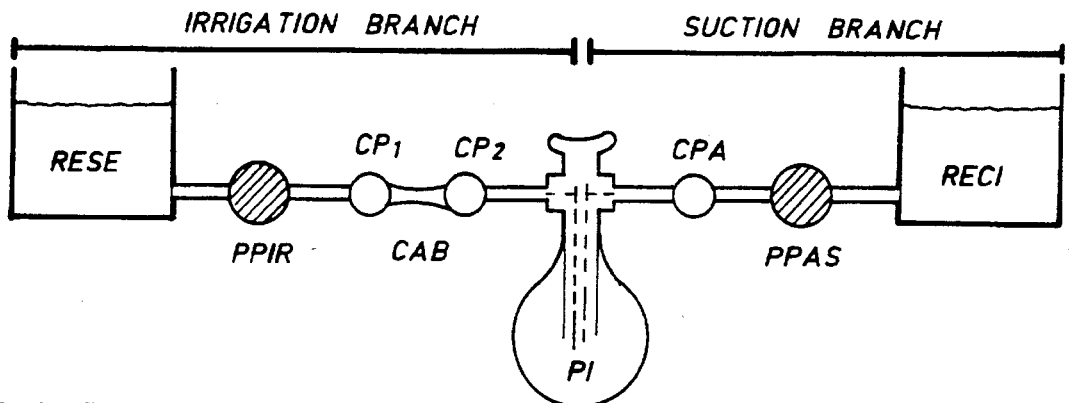
FIG. 6 is a simplified schematic of the circuit and its irrigation and suction branches.
Figure 10:
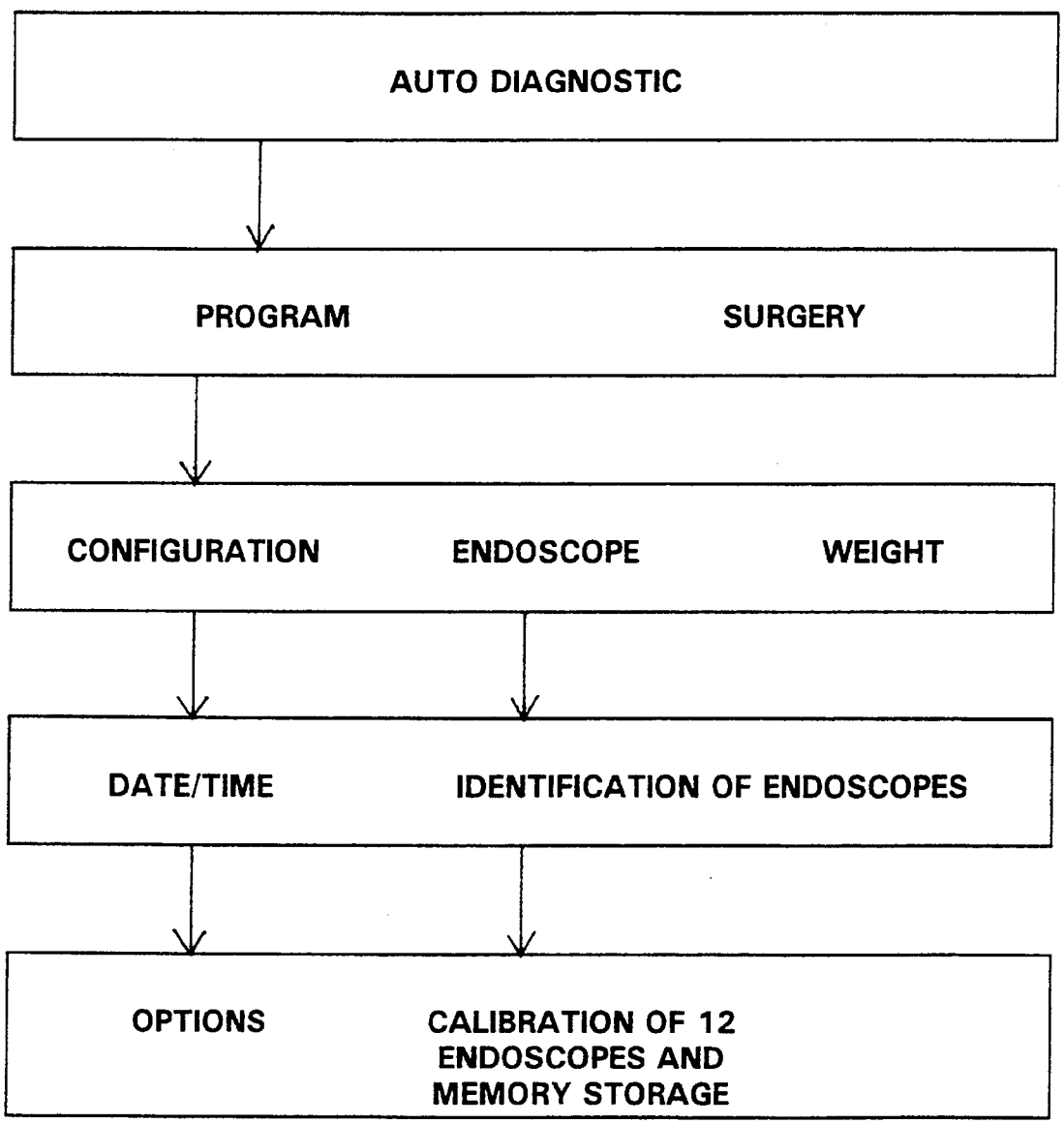
FIG. 10 is a general synoptic chart showing how the apparatus is implemented and used.
Figure 11:
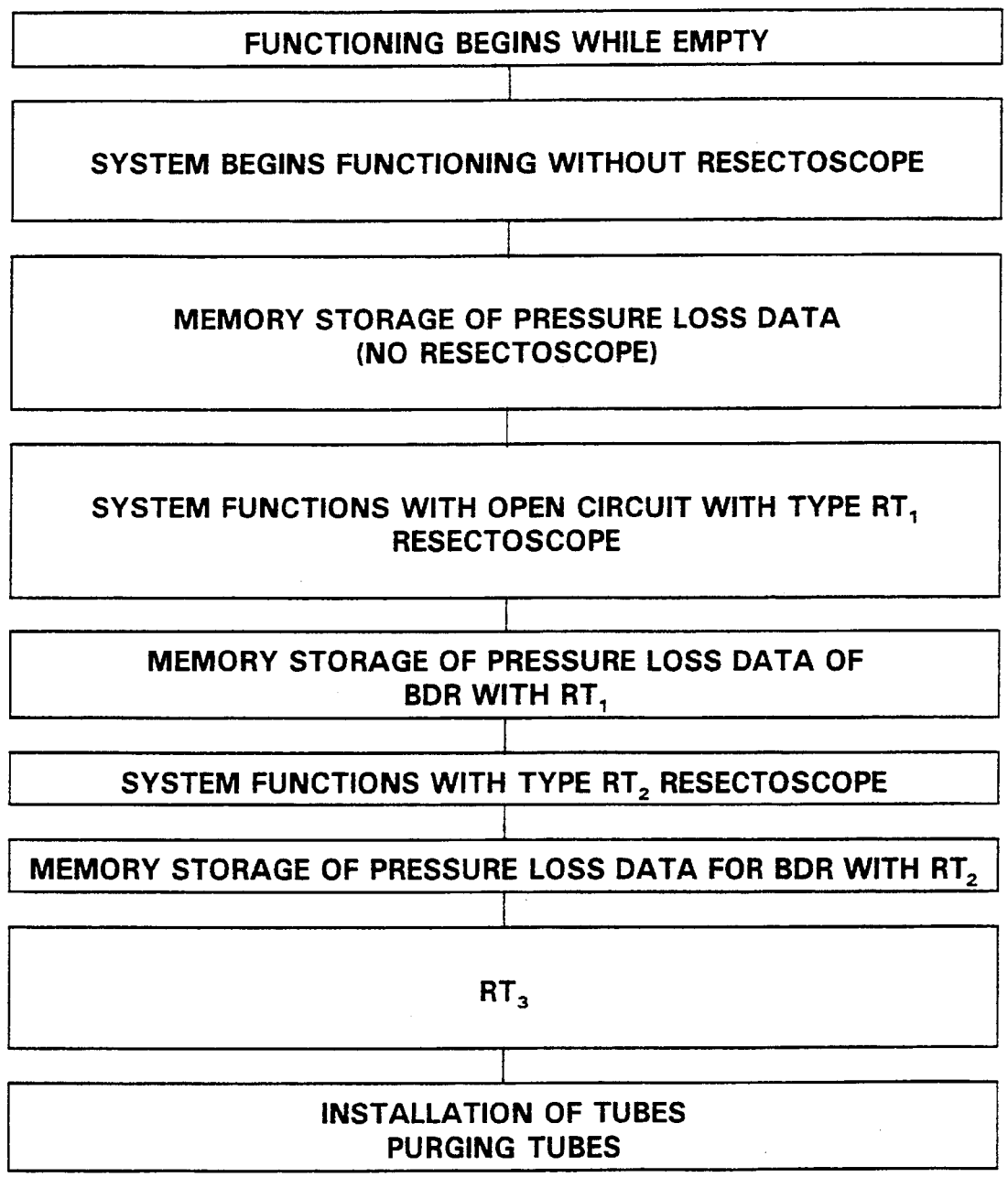
FIG. 11 is an organizational diagram showing how the apparatus is calibrated to conform to the principal types of existing resectoscopes.

To accomplish this, central processor/control unit UCCG has a CALIBRATION function which it performs during the initial phase known as the CALIBRATION phase, as shown in FIGS. 5, 10 and 11. Calibration is accomplished by storing the discrete values of pressure loss in the circuit, branch by branch, while the instrument is outside the cavity, for each instrument of the various types RT1, RT2 . . . , RTi . . . RTn that can be adapted to the apparatus for the particular type of surgery for which it is designed.

Theoretically, this initial CALIBRATION sequence is performed once for each type of surgery for which the device is designed, thereby eliminating the need for long, tedious preparatory procedures or at the very least, reducing them to one simple regulation.

This can also be done based on mathematical modeling of the pressure loss curve. In this case, one need modify only one specific parameter relating to the selected resectoscope.

First the circuit is arranged as shown in FIG. 5. According to this arrangement, the anterior extremity of the instrument with the irrigation and suction orifices is placed in a receptacle holding liquid clarificant or water, which then reverses hydraulically on itself. Thus, a hydraulic short circuit occurs. The apparatus then performs with liquid clarificant or water at the various irrigation flow rates that will be used, for example, from 0 to 500 ml/mn, according to discrete values incremented by 10 ml/mn each time, or less, depending upon the precision required. The pressure variations are furnished by sensors CP1 and CP2 (or $\Delta P = P1-P2$) and curves representing the pressure loss as shown in FIG. 7, are stored separately for each branch of the irrigation and suction networks.

Since the curves representing the pressure loss within the irrigation and suction circuits outside the cavity can be accessed, they can be compared with the values shown during the surgical procedure, that is, value by value for a given point during use. These pressure loss values can also be annulled. To do this, the software calculates the correction by compensation-annulment. This is done for each point and for each curve by subtracting an identical value so as to annul the pressure loss specific to the circuit outside the cavity and yielding only the internal cavity pressure value PI during actual use and surgical intervention.

Figure 7:
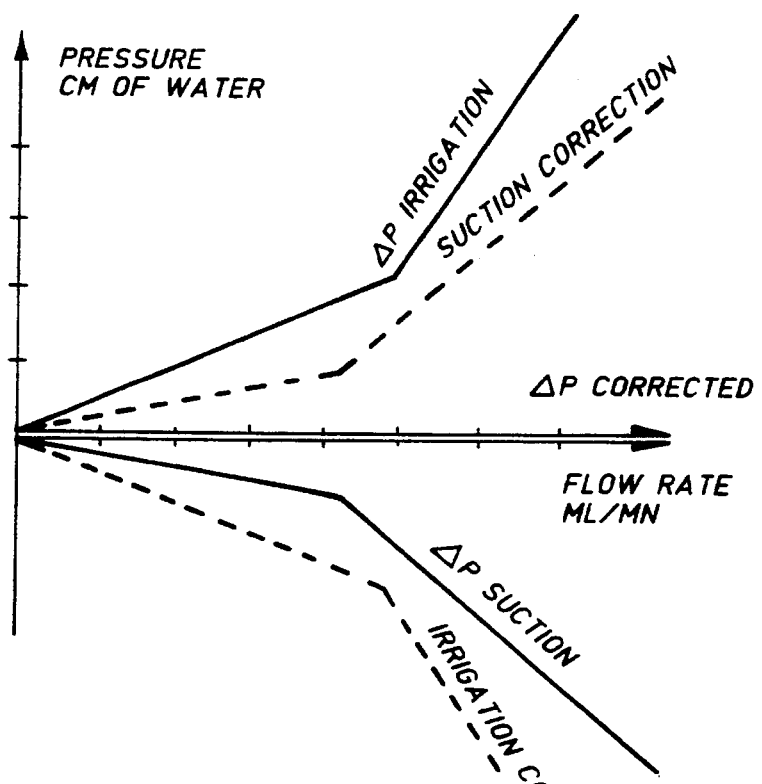
FIG. 7 is a composite graph which illustrates the compensation-annulment principle of pressure loss used within the apparatus.

FIG. 7 demonstrates this method.

The reason the symmetrical curves are shown in negative values for the irrigation and suction networks is to show how they vary from this component specific to the empty circuit, that is, outside the cavity.

As indicated, the reason for the compensation-annulment is to achieve a straight, nil pressure line for each branch, whatever the flow rate may be, and thus to determine directly the value of internal pressure PI within the cavity.

Once the incidence of pressure loss within the empty irrigation and suction networks is discounted, with all other factors remaining equal, what remains is the pressure originating from the cavity, that is, interior cavity pressure.

In the case of mathematical modeling of the weight loss curves with the instrument outside the cavity, the acquisition phase disappears. It is replaced by simply introducing into the mathematical formula the new value of the parameter characterizing the instrument.

The principle according to which the device functions is based on permanent knowledge of the real, exact pressure PI within the cavity and eliminating the factor of pressure loss within the circuit outside the cavity.

The most important factor is the actual internal pressure PI within the cavity, that is, the pressure which results after all external and internal factors have been accounted for: liquid clarificant, urine, blood.

This pressure value PI is the basis upon which the software controls how the apparatus performs.

This principle may be demonstrated as follows, with reference to FIGS. 10, 11 and 12.

In the network consisting of the circuits, the signal processor and calculating means, the calculated internal pressure value, PI, is established as follows:

The pulsating pressure signal provided by the two upstream pressure sensors CP1 or CP2, characteristic of a peristaltic pump, is filtered and modulated so that a continuous significant component can be extracted.

This continuous component is used to calculate interior cavity pressure while neutralizing the incidence of pressure originating from the pressure losses PC caused by the instrument and the intermediate circuit.

The central processor/control means UCCG is designed to activate the apparatus in three specific modes which are, respectively, the PURGE program, the CALIBRATION program and the UTILITY program.

During the PURGE program the irrigation and suction robes are interconnected and a purging fluid flows through them to clean them.

During the CALIBRATION program, the following occurs:

The CALIBRATION curves differ from one instrument to another because the canal diameters vary. The three curves shown correspond to different diameters RT1, RT2 and RT3 of three distinct instruments that are adaptable for use with the device of the invention.

The third pressure sensor CPRE is necessary to provide a reference pressure measurement which, in a urological or gynecological application, might be the abdominal pressure or the pressure corresponding to the height of the operating table holding the patient, which is read at point PPRE.

Figure 3:
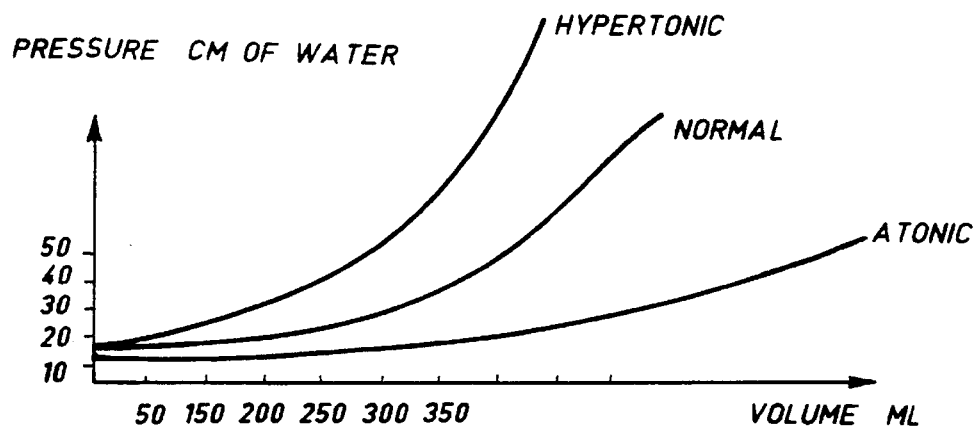
FIG. 3 is a graph with curves illustrating the elasticity of three characteristic bladder types—hypertonic, normal and atonic—and illustrating the rise in pressure within the bladder as a function of the volume of liquid therein.
Figure 4:
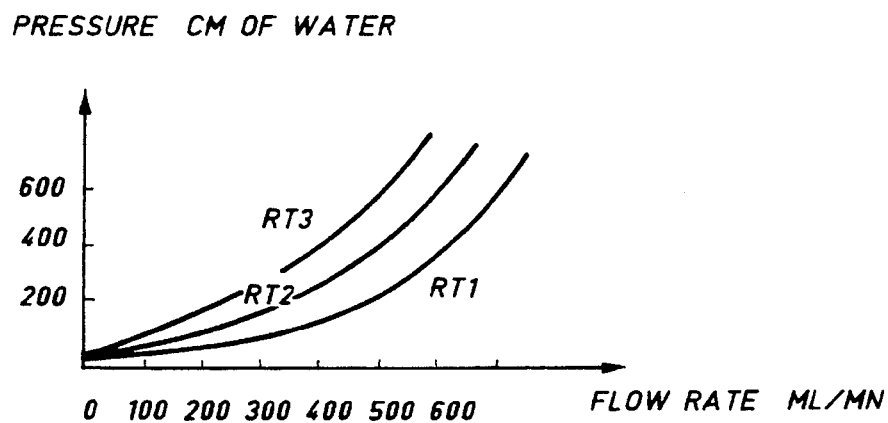
FIG. 4 is a graph with curves illustrating the pressure loss within the irrigation network outside the cavity for three resectoscopes RT1, RT2 and RT3, each having conduits of different diameters.

When the UTILITY phase begins, the zero settings of sensors CP1, CP2 and CPA are adjusted once the instrument and the reference sensor CPRE have been placed at the same height as the organ where intervention will take place. The surgeon introduces the instrument into the cavity and the organ is filled, using either manual or automatic control. Flow rate, volume and maximum pressure are regulated. The pressure/volume curve furnishing precise data regarding the extent to which the organ is "inflated" is visible on a screen connected to the central processor and a control means UCCG or on a printer. The curve shows that as the organ (generally pouch-like, as in the case of a bladder) is being filled, interior pressure increases slightly until the organ is full and until supplemental liquid injection has dilated it. At this moment dilating the walls causes a rapid, discernible pressure increase (FIG. 3).

The surgeon can determine the working parameters, that is, the maximum and minimum volumes of physiological liquid clarificant to be injected either into the cavity, or at or near the intervention site, as a function of the maximum and minimum pressures which should not be exceeded. In order to maintain these working parameters, the suction circuit evacuates excess fluid.

Figure 8:
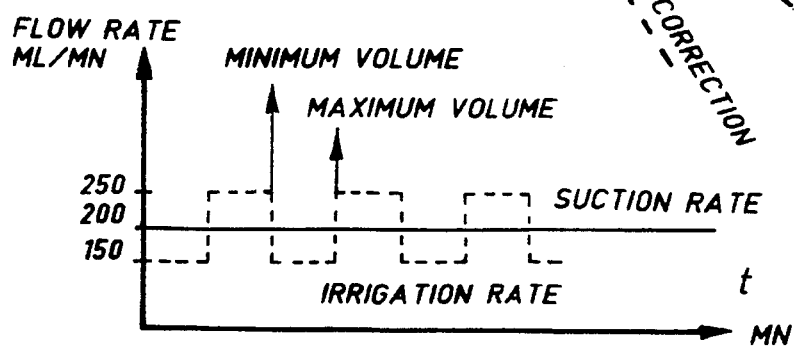
FIG. 8 is a schematic curve showing one example of how the irrigation and suction flow rates are controlled for a normal range of pressure as a function of time.

FIG. 8 shows one example of the curves representing the suction flow rate (dashed lines) and the irrigation flow rate (solid lines) as a function of time. Flow regulation is accomplished either by providing an irrigation rate that is equal to the suction flow rate at constant volume, or by regulating on the basis of minimum and maximum volumes. This example is shown in FIG. 8.

Thus, pressure is automatically regulated within a range of pressures considered to be working pressures. This working range consists of from 7 to 12 cm of water, as shown in FIG. 9.

This is the normal working mode, the auto-regulating pressure system, i.e., the range of internal pressures within which the apparatus regulates pressure automatically to bring it back to or around the assigned value.

When the pressure increases due to partial or total obstruction of the suction orifice (contact by the suction orifice of the instrument with the wall of the urinary tract), possibly caused when the end of the instrument is withdrawn because the surgeon wishes to control the resection procedure or for whatever reason, then the intermediate pressure in excess of 12 cm of water causes the system to switch to the non-regulated mode, which is progressively compensated for by increased suction flow rate and signaled by audible beeps BS1 and BS2.

This is the higher pressure operating mode, characterized by a simple compensation for flow rates and a variable rhythm audible signal TR1 and TR2.

As the chart in FIG. 9 shows, this is divided into two
- phases: a first phase in which the irrigation flow rate is limited to 200 ml/mn and the suction rate increases progressively with pressure, characterized by an audible beep BS1 repeated at a rate of TR1=10 seconds;
- a second phase in which the irrigation rate is always limited to 200 ml/mn and the suction rate achieves its maximum of 500 ml/mm, characterized by an audible beep BS2 repeated at a rate of TR2=3 seconds.

For the duration of the procedure, if the pressure measured by the two sensors respectively attached to the irrigation network and the suction networks varies by more than 10%, the direction in which the suction pump rotates is reversed so that for about 5 seconds liquid is injected into the suction network to flush out the solid particle obstructing the suction circuit and which is the actual cause of the pressure variation. If the problem persists, the pumps are stopped to prevent excessive pressure buildup within the organ.

The two peristaltic pumps PPIR and PPAS which are designed to function either automatically or manually may be either independent or may consist of a dual pump. The irrigation circuit is permanently verified by the measurements which are continuously being taken(weight, volume, pressure, flow rate). These same measurements are performed on the suction circuit and in addition, a comparative verification of both circuits is made Periodically measuring the weight differences of the liquids injected and recovered (suction plus recovery) yields the weight of incoming blood and urine in the cavity and thus, taking density into account, gives the volume of incoming fluid expressed as follows:

V injected–V recovered=V incoming

The volume measurements associated with the conductimetric sensor give the approximate quantity of liquid clarificant absorbed by the circulatory system.

At the end of the procedure, a manual command empties the cavity. The suction circuit of the instrument closes. The tip of the suction tube is connected to the main tip of the instrument. The solid particles or fragments remaining from the procedure within the organ may be recovered for later analysis.

The printed surgical report furnished by the computer UCCG after surgery provides a written record of the surgical conditions which could serve as evidence if required.

The surgical report classifies the following data:

time data: date, time surgery began and ended;

internal cavity pressure readings;

flow rates;

weights of irrigation and suction fluid.

Other information could be incorporated, such as:

a pressure curve representing work/duration of intervention;

indication of the minimum and maximum volumes during work;

the extent of hemodilution and evolution thereof over time;

a precise indication of blood loss during the procedure and, generally speaking any useful information about the procedure and conditions affecting it.

Thus, after surgery, pressure and flow rate at any given time can be specified, as well as the amount of bleeding and other information about the quality of the procedure.

Such a surgical report has no legal validity in FRANCE since it is not yet recognized as such. However, it can serve as a means of simple proof in any instance where responsibility or expertise are at issue. Therefore, it has great scientific and medical value.

The present invention is not limited to the embodiments described, but extends to any modification which may be obvious to one skilled in the art.

What is claimed is:

1. Apparatus for the controlled irrigation and suctioning of a liquid clarificant in a cavity or a natural passageway in the human body during a surgical procedure with an endoscopic surgical instrument having an injection conduit for injecting liquid clarificant into the cavity or natural passageway and a suction conduit for suctioning liquid clarificant from the cavity or natural passageway, the apparatus comprising:

an irrigation branch for connection to the injection conduit of the instrument and a suction branch for connection to the suction conduit of the instrument, each of said branches having at least one pressure sensor and a pump;

the irrigation branch comprises, in sequence commencing from an end of the irrigation branch remote from the instrument: (a) a reservoir (RESE) for storing the liquid clarificant, the reservoir being supported by a first weighing means (DISPE1) for weighing the liquid clarificant contained in the reservoir (RESE); (b) a peristaltic irrigation pump (PPIR) with a flow regulator; and (c) a pressure differential sensor block (BCDP) formed by a pair of irrigation pressure sensors (CP1 and CP2), interconnected by a calibrated Venturi conduit (CAB), for measuring a respective pair of irrigation pressure values (P1 and P2);

the suction branch comprises, in sequence, commencing adjacent the outlet of the instrument: (a) a pressure sensor (CPA) to measure downstream pressure (P3); (b) a peristaltic suction pump (PPAS) with a flow regulator; (c) a recovery pump (POR) connected to a recovery branch (BRE), which is in turn connected to a collection device on the operating table; (d) a conductimetric cell (CECO) which measures hemodilution; and (e) a receptacle (RECI) for recovering liquid clarificant, the receptacle (RECI) being supported by a second weighing means (DISPE2) for weighing the liquid clarificant recovered by the receptacle;

the entire system being connected to a central processing and control unit (UCCG) having a flowmeter measurement device (UMDI) for determining an irrigation flow rate (PPIR) in the irrigation branch from the difference between the pair of irrigation pressure values (P1 and P2) measured by the pair of irrigation pressure sensors (CP1 and CP2), and a control circuit (CIRP) for controlling the irrigation pump in response to the determined irrigation flow rate (PPIR) and thereby controlling an interior cavity pressure (PI) inside the cavity or natural passageway; and the first and second weighing devices (DISPE1 and DISPE2) are each connected to means for comparing the measurement results of each device with each other, and a reference pressure sensor (CPRE), for measuring a reference pressure, is connected to the processing and control unit (UCCG) in order to compare the measured reference pressure with the pressures measured by the other pressure sensors and thereby determine corresponding relative pressures with regard to the reference pressure.

2. An apparatus according to claim 1 wherein the central processor (UCCG) comprises circuits for filtering, preparing and processing signals generated by the irrigation flow pressure sensors (CP1 and CP2).

3. An apparatus according to claim 1 wherein the means for comparing the measurement results from each of the first and second weighing devices (DISPE1 and DISPE2) is a measurement differential circuit (CIRDI).

4. A method for the controlled irrigation and suctioning of a liquid clarificant in a cavity or a natural passageway in the human body during a surgical procedure with an endoscopic surgical instrument having an injection conduit for injecting liquid clarificant into the cavity or natural passageway and a suction conduit for suctioning liquid clarificant from the cavity or natural passageway, using a control apparatus having an irrigation branch for connection to the injection conduit of the instrument and a suction branch for connection to the suction conduit of the instrument, said method comprising the steps of:

calibrating the apparatus for each endoscopic surgical instrument which is adaptable to the apparatus by storing information regarding pressure loss within the irrigation branch and pressure loss within the suction branch for each instrument, when each instrument is located outside the cavity or natural passageway;

calculating an internal pressure (PI) within the cavity or natural passageway, which forms the basis for pressure regulation, by using the stored pressure losses regarding when the instrument is outside the cavity or natural passageway to correct for pressure loss in the irrigation branch and suction branch when the instrument is inside the cavity or natural passageway during surgery.

5. A method according to claim 4 comprising calculating the interior pressure (PI) within the cavity or natural passageway using the stored calibration pressure loss data.

6. A method according to claim 4 comprising calculating the interior pressure (PI) by generating a pressure loss curve from the stored calibration pressure loss data for each of the calibrated instruments and then calculating the interior pressure using the pressure loss curve.

7. A method according to claim 4 where the calibration step comprises hydraulically closing the instrument on itself by placing the extremities of the irrigation branch and the suction branch in a container holding the liquid clarificant and operating the apparatus in the entire range of the apparatus functions.

8. A method according to claim 4 comprising generating a mathematical model representing the pressure loss curves during performance outside the cavity for each branch, and using the mathematical model to calculate the internal pressure (PI) during surgery.

9. A method according to claim 4 wherein the calibration step comprises modifying an operating parameters for the instrument for one of the irrigation branch and the suction branch.

10. A method according to claim 4 comprising regulating the interior pressure (PI) within the cavity by fixing the irrigation flow rate and controlling the suction pump flow rate.

11. A method according to claim 4 comprising determining the pressure loss in the irrigation branch by measuring a pressure difference between two irrigation branch pressure sensors (CP1 and (CP2) interconnected by a calibrated conduit (CAB).

12. A method according to claim 11 comprising filtering, modulating and processing a signal corresponding to the pressure difference $\nabla P=P1-P2$ delivered by sensors (CP1 and CP2) and performing a correction on the basis of this value to calculate the internal pressure (PI) prevailing in the cavity.

13. A method according to claim 4 comprising regulating the irrigation flow rate such that the calculated interior pressure (PI) within the cavity remains within a working rage extending from 7 to 12 cm of water.

14. A method according to claim 4 comprising causing a temporary increase in irrigation-suction by activating an exterior control means.

15. A method according to claim 4 comprising collecting the liquid recovered by the collection device on the operating table and adding the collected liquid to the recovered liquid clarificant in the recovery device.

* * * * *